US00PP35081P2

(12) United States Plant Patent
Halladin

(10) Patent No.: US PP35,081 P2
(45) Date of Patent: Apr. 4, 2023

(54) MAPLE TREE NAMED 'INAG-E61'

(50) Latin Name: ***Acer pseudosieboldianum* x *Acer palmatum***
Varietal Denomination: INAG-E61

(71) Applicant: Early Morning LLC, Boring, OR (US)

(72) Inventor: Paul H. Halladin, Boring, OR (US)

(73) Assignee: Early Morning LLC, Boring, OR (US)

( * ) Notice: Subject to any disclaimer, the term of this patent is extended or adjusted under 35 U.S.C. 154(b) by 0 days.

(21) Appl. No.: 17/958,742

(22) Filed: Oct. 3, 2022

(51) Int. Cl.
*A01H 5/00* (2018.01)
*A01H 6/00* (2018.01)

(52) U.S. Cl.
USPC ..... Plt./224

(58) Field of Classification Search
USPC ..... Plt./216, 224
See application file for complete search history.

*Primary Examiner* — Karen M Redden
(74) *Attorney, Agent, or Firm* — Weatherly IP Solutions, LLC; James M. Weatherly

(57) ABSTRACT

A new and distinct variety of Maple tree being small to moderate-sized with red leaves, hardy in USDA Zones 4 to 8, and having an upright, narrow, oval habit, is disclosed.

7 Drawing Sheets

Genus and species: *Acer pseudosieboldianum* x *Acer palmatum.*

Denomination: 'INAG-E61'.

BACKGROUND

'INAG-E61' is a new and distinct variety of Maple tree. 'INAG-E61' originated from a tree breeding program started in 1997 with the goal of expanding the cold tolerance range of Japanese Maple trees to include USDA Zone 4. The focus has been on red foliage color.

The general term "Japanese maples" applies to species, forms, and cultivars within Section and Series Palmata including native Japanese species *Acer palmatum, japonicum, shirasawanum*, and *sieboldianum* and two not native species, the West Coast North American species *Acer circinatum* or Vine maple and *Acer pseudosieboldianum* or Korean maple.

*Acer pseudosieboldianum* is the foundation breeding genetics used for enhancing hardiness. This species is native from the Korean peninsula north into the biodiverse forested Ussuri river region of Eastern China and Russia, a region spared from past glaciation enabling long periods of uninterrupted species development from a former warm climate to the current cold dry winter climate. *Acer pseudosieboldianum* successfully grows in the Upper Midwest region of USDA zone 4 with some seedling and cultivar success in USDA zone 3. Besides hardiness, Korean maple has features of sun tolerant vibrant green summer foliage, outstanding multicolored fall foliage, but as a garden tree the typically marcescent leaves and coarse, open, erratic branching and unpredictable habit is a detraction.

The species native to Japan: *Acer palmatum, japonicum, shirasawanum*, and *sieboldianum* have long been garden worthy trees with hundreds of years of human selection and refinement. These species and selected cultivars are USDA Zone 5 or 6 or 7 and as such are either marginal or not hardy as garden trees for much of North America, hence, the breeding combination of superior garden quality Japanese maple trees crossed with the cold hardy genetics from *Acer pseudosieboldianum.*

In 1997, a controlled breeding program was started in a greenhouse in Boring, Oreg. using Korean maple seedlings (female parent) with *Acer palmatum* 'Nuresagi' unpatented (male parent). 'Nuresagi' is an upright Japanese maple tree with deep-purple-red, palmate, 5-7 lobed leaves, and hardy to USDA Zone 5. Seedlings from this cross were grown and evaluated with one seedling designated 'E7' showing red pigmented new growth that matures green. 'E7' was propagated and later named NORTH WIND 'Is1NW' (not patented). This cultivar has been found to be USDA Zone 4 hardy, but the red color needed further improvement. In spring 2006 NORTH WIND 'Is1NW' was used as the female seed parent for 'INAG-E61' and was open-pollinated. The male parent is unknown but adjacent to the female parent tree were three same-aged, red-leafed hybrid selections identified as 'E3', 'E4', and 'E26'. Seeds from the open-pollination were collected Fall 2006 and planted April 2007 and germinated June 2007. The best seedlings from this cross were grown for long term evaluation in a testing location in Boring, Oreg. In July 2016 'INAG-E61' was first identified. First hardiness screening test December 2016.

'INAG-E61' was first propagated by grafting in August 2016 onto *Acer palmatum* seedling rootstock (unpatented). 'INAG-E61' reproduces true to type in successive generations of asexual reproduction via grafting onto *Acer palmatum* seedling rootstock (unpatented).

SUMMARY

The following are the most outstanding and distinguishing characteristics of this new variety when grown under normal horticultural practices in Boring, Oreg.

1. A small to moderate-sized Maple tree with red leaves;
2. Hardy to USDA Zones 4 to 8; and
3. Having an upright, narrow, oval habit.

DESCRIPTION OF THE PHOTOGRAPHS

This new *Acer* tree is illustrated by the accompanying photographs which show the plant's overall plant habit including form, trunk, and foliage. The photographs were taken outdoors in Boring, Oreg. with dates indicated. The colors shown are as true as can be reasonably obtained by conventional photographic procedures.

DETAILED DESCRIPTION

Figure 1:
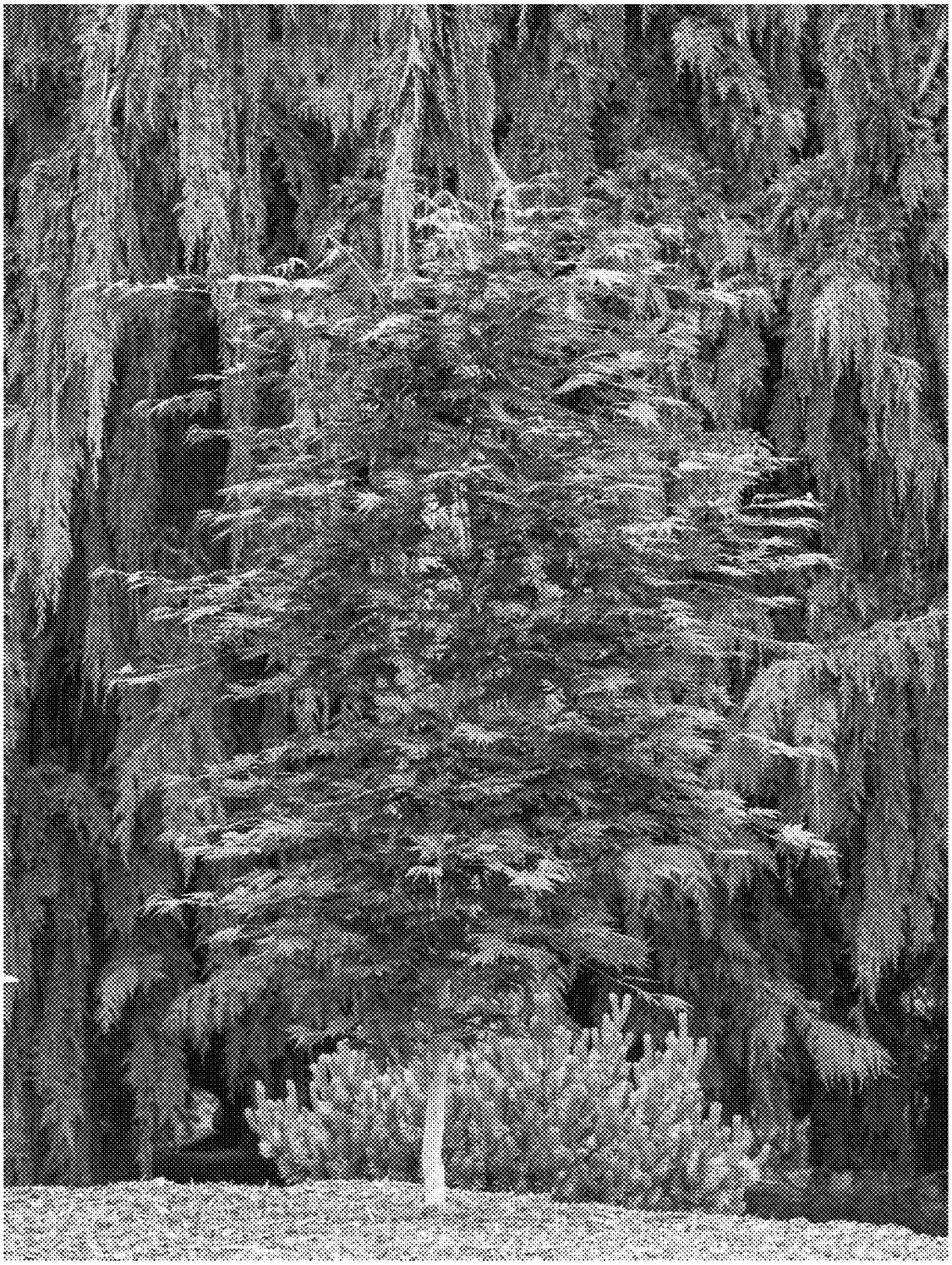
FIG. 1 shows a 6-year-old tree of 'INAG-E61' in the foreground on May 26, 2022.
Figure 2:
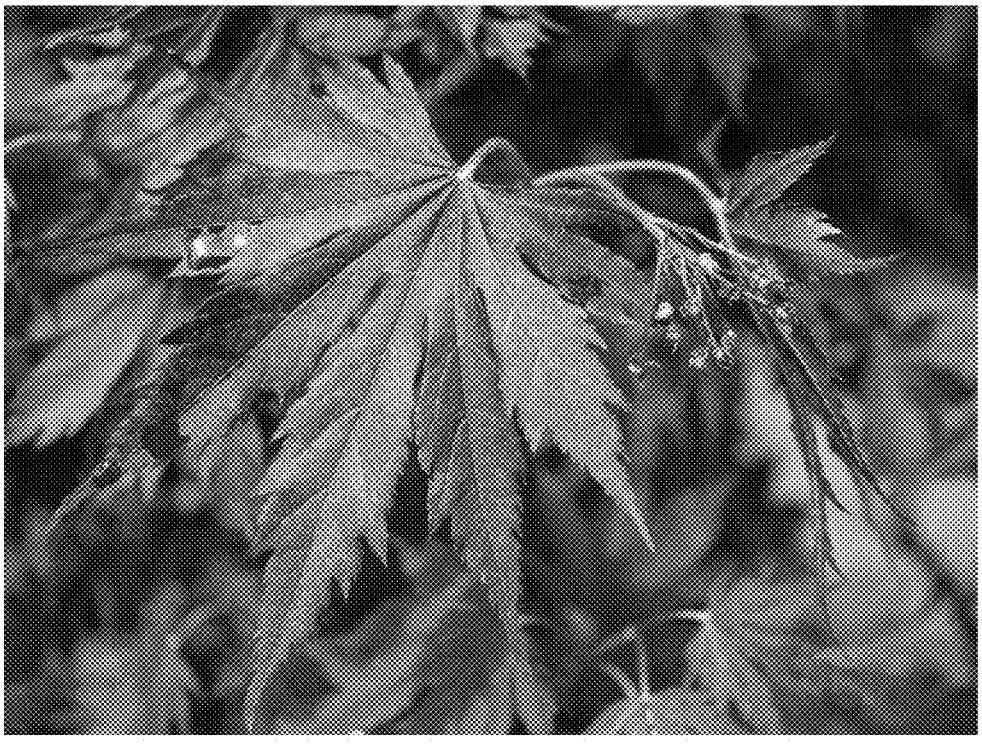
FIG. 2 shows a close-up of the spring foliage and the flowers of a 5-year-old tree of 'INAG-E61' on May 7, 2021.
Figure 3:
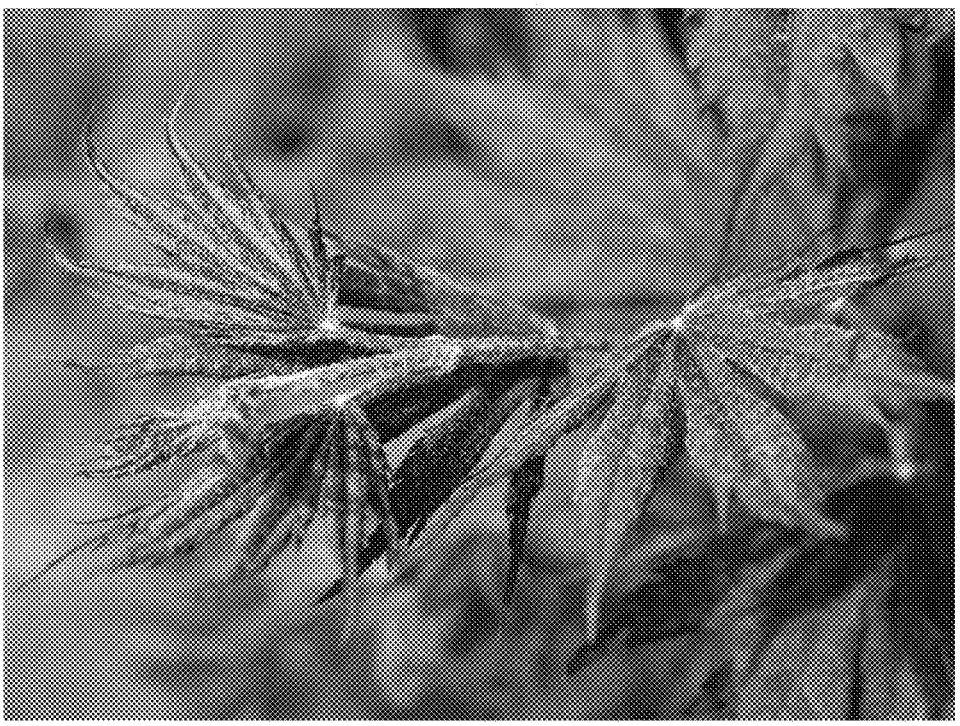
FIG. 3 shows a close-up of the immature spring foliage with pubescence of a 5-year-old tree of 'INAG-E61' on Apr. 29, 2021.
Figure 4:
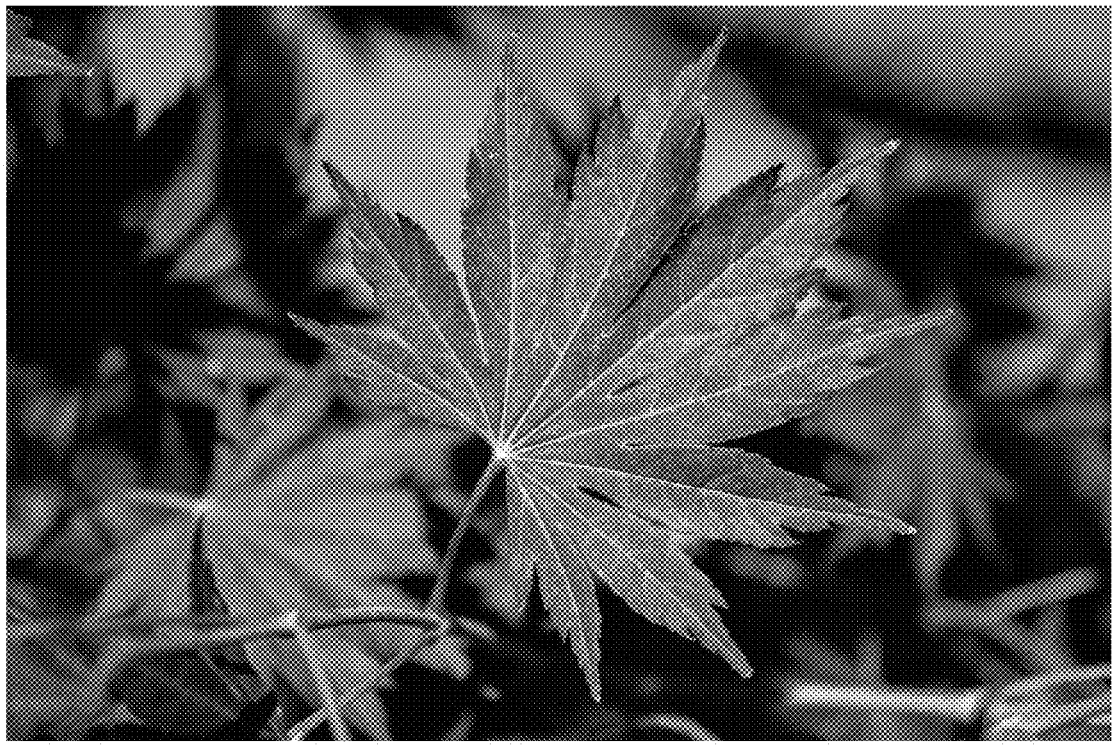
FIG. 4 shows a close-up of the summer foliage of a 14-year-old tree of 'INAG-E61' on Jun. 24, 2021.
Figure 5:
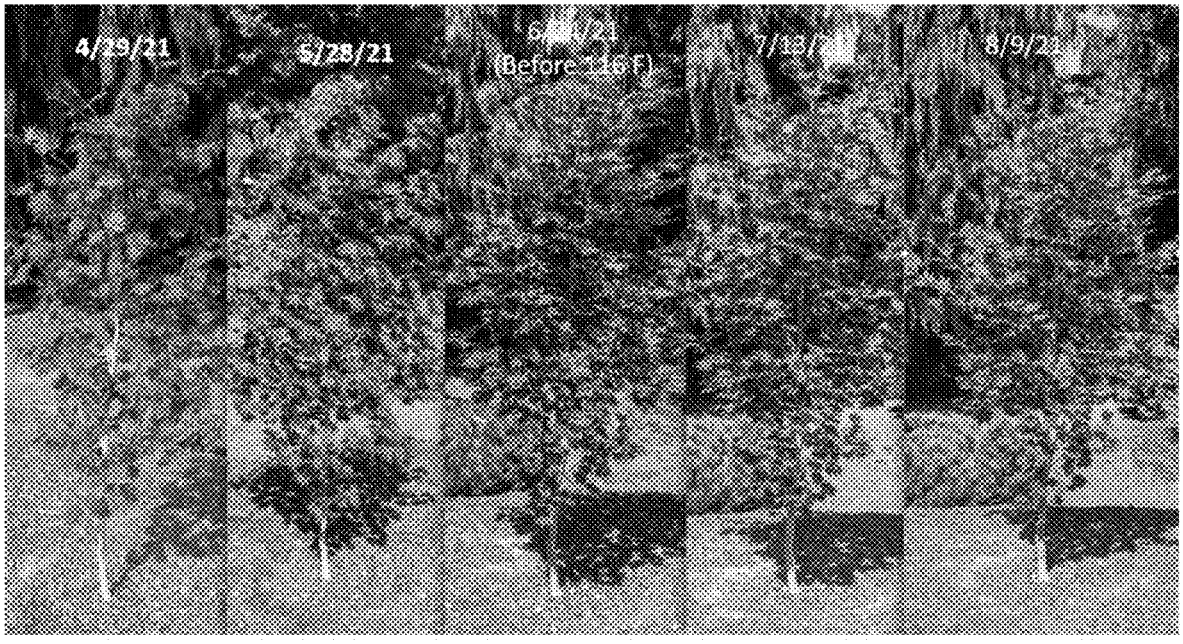
FIG. 5 shows the progression of the foliage color of a 5-year-old tree of 'INAG-E61' from April to August 2021.
Figure 6:
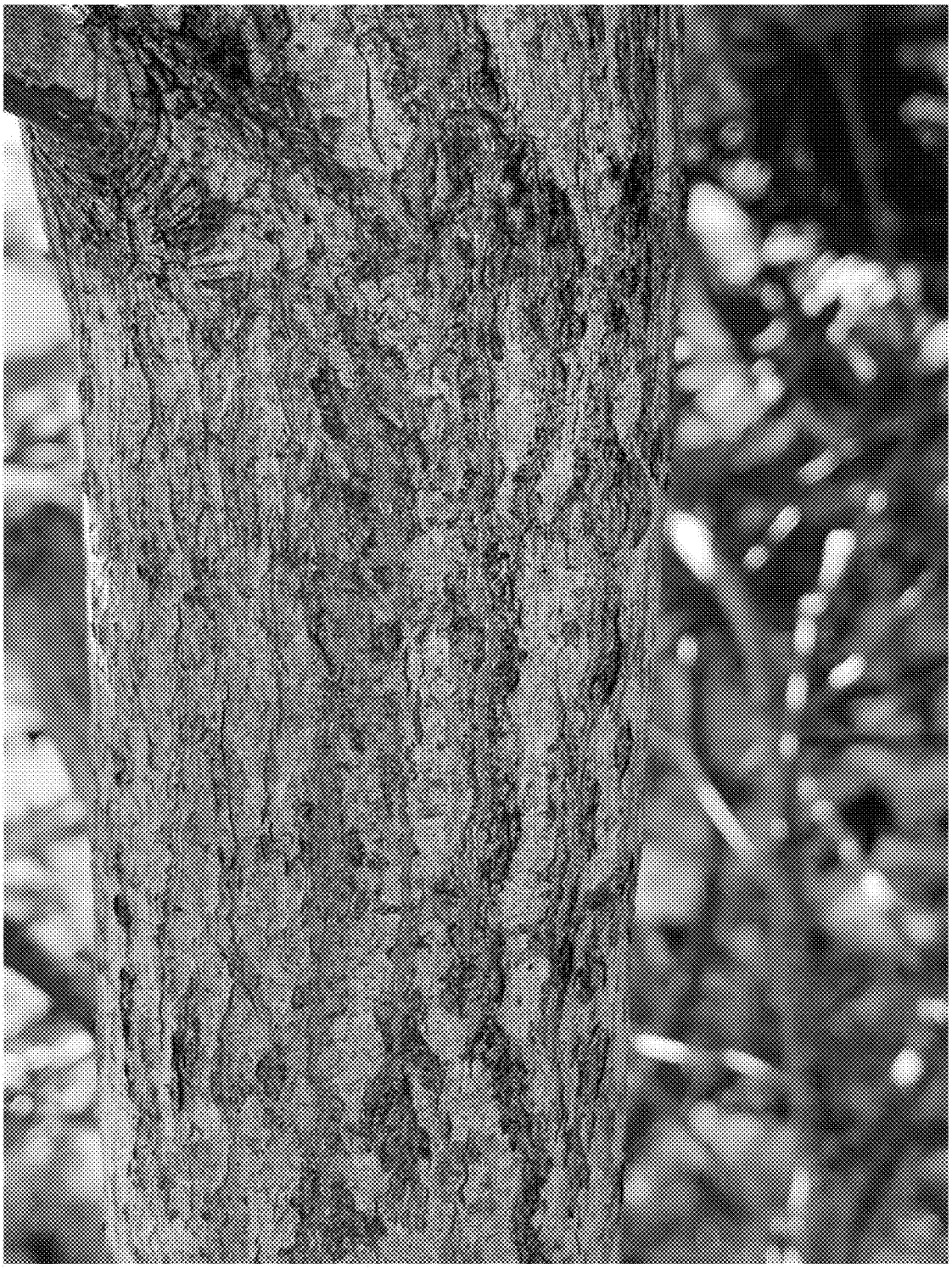
FIG. 6 shows a close-up of the bark from a 15-year-old tree of 'INAG-E61' on Sep. 7, 2022.
Figure 7:
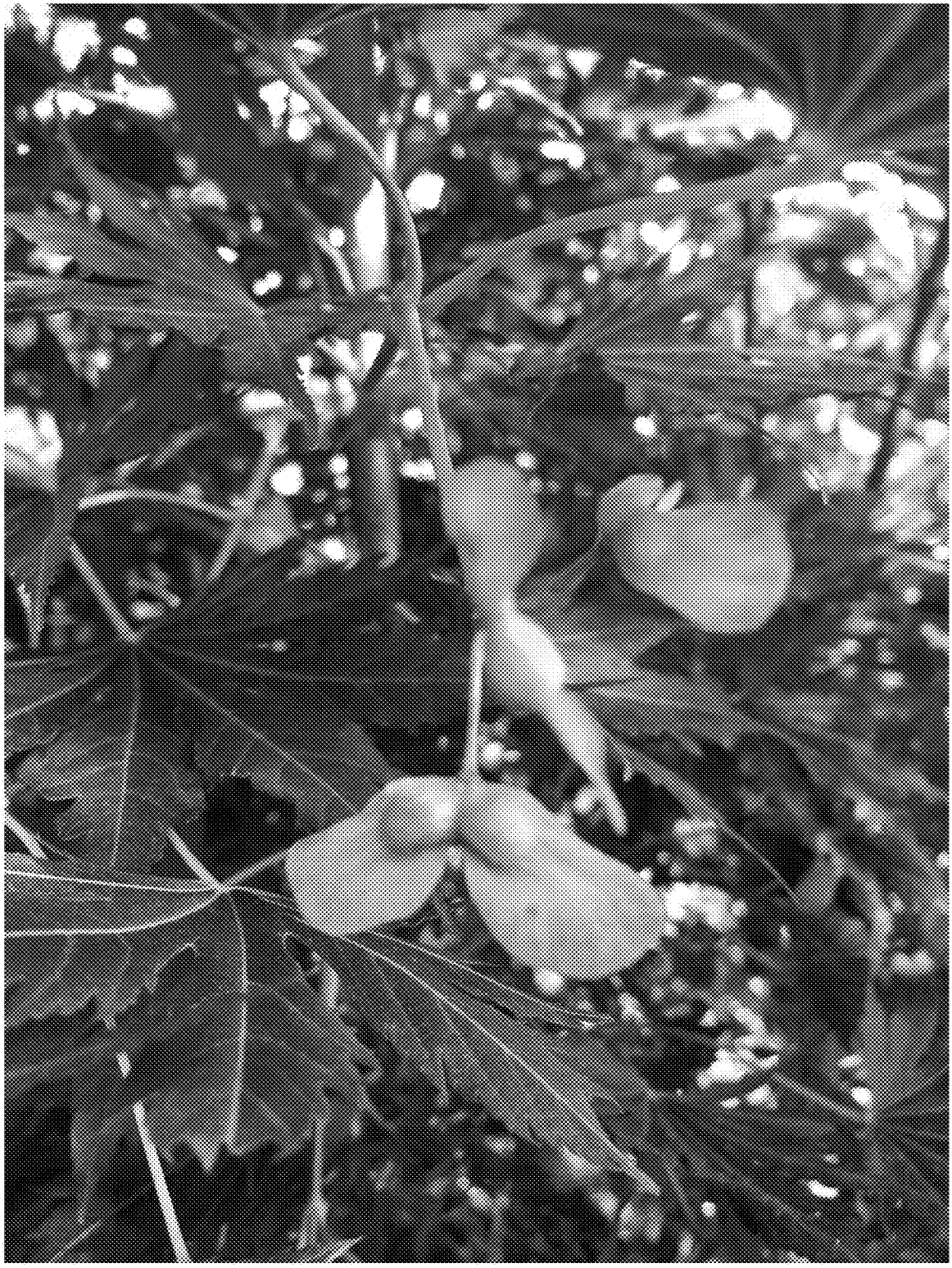
FIG. 7 show a close-up of the samara from a 12-year-old tree of 'INAG-E61' on Aug. 2, 2019.
Figure 8:
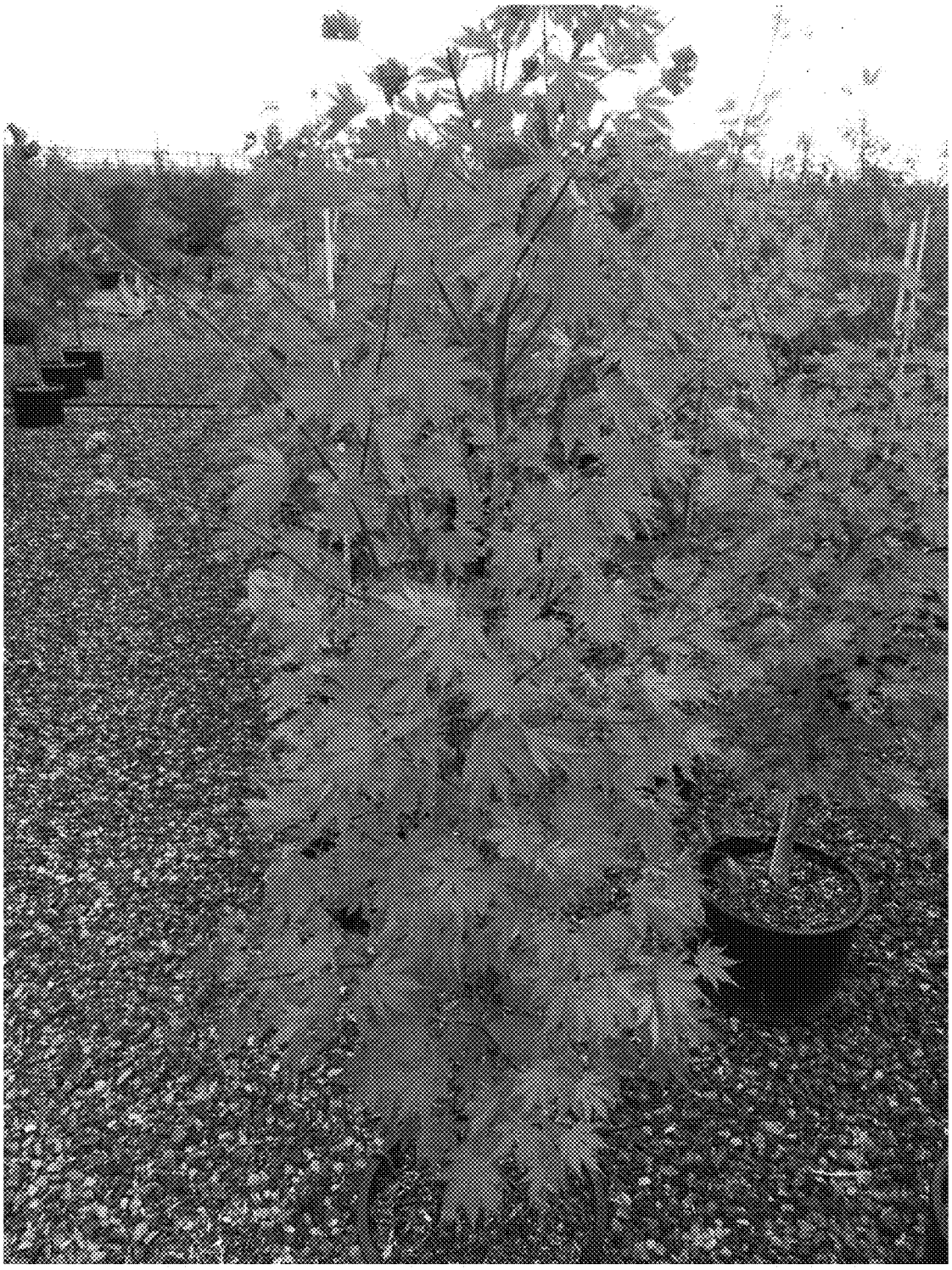
FIG. 8 shows a whole 4-year-old tree of 'INAG-E61', including the fall foliage on Oct. 19, 2021.
Figure 9:
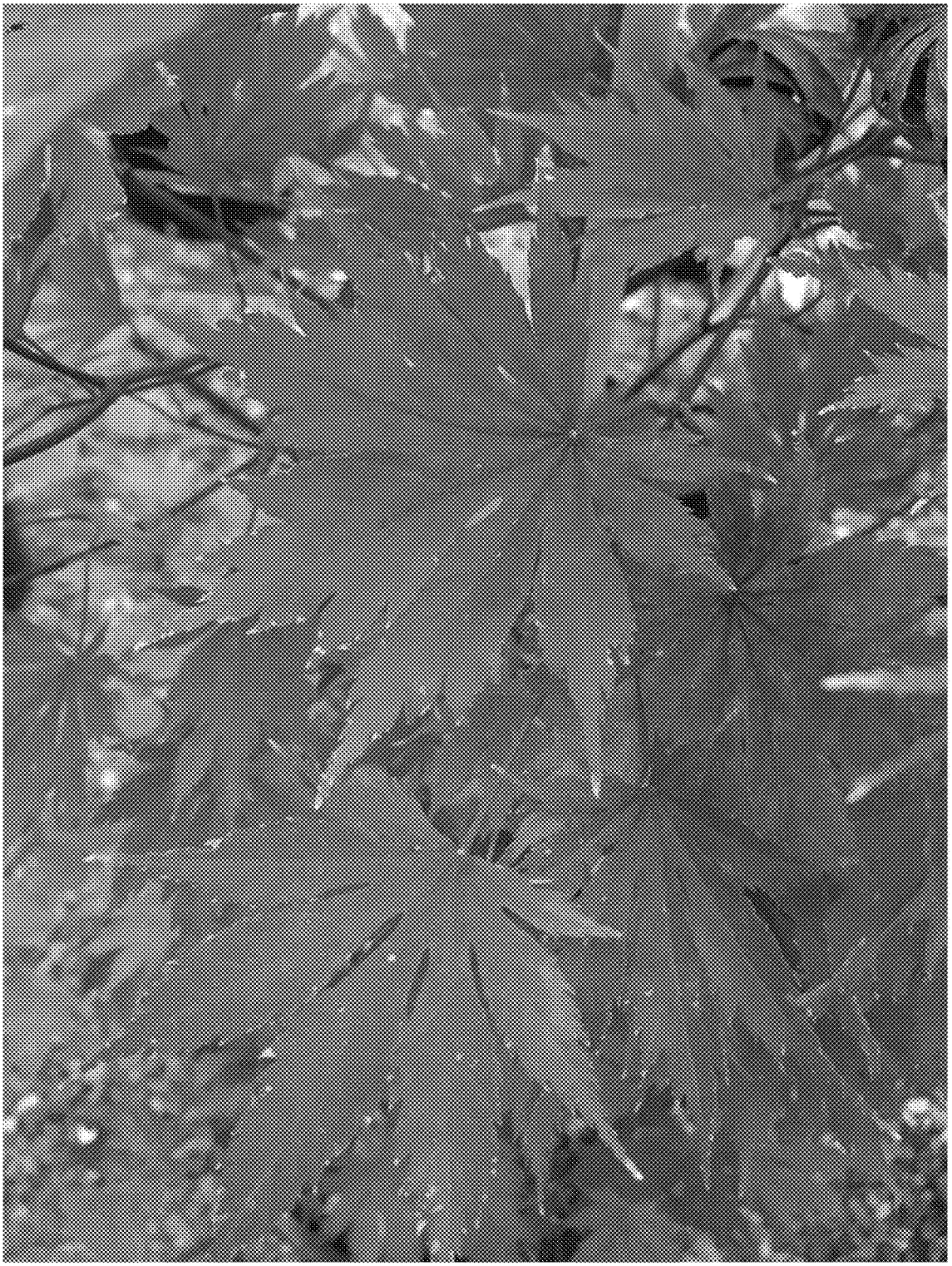
FIG. 9 shows a close-up of the fall foliage Oct. 19, 2021 of the tree of FIG. 8.

The following detailed descriptions are for the distinctive characteristics of 'INAG-E61'. The data which define these characteristics were collected outdoors in Boring, Oreg. in August 2022 (unless noted) on 6-year-old and 15-year-old trees in Boring, Oreg. Color references are to The R.H.S. Colour Chart of The Royal Horticultural Society of London (R.H.S.) 2001, except where general terms of ordinary dictionary significance are used.

Classification:

*Family.*—Sapindaceae.

*Botanical.*—*Acer pseudosieboldianum* x *Acer palmatum.*

*Denomination.*—'INAG-E61'.

Tree:

*Type.*—Deciduous.

*Shape.*—Upright, narrow, oval.

*Growth and branching habit.*—Small to moderate-sized single stem garden tree; upright, and slightly spreading; well-ordered branch pattern; full-leafed tree.

*Propagation type.*—Grafting onto seedling *Acer palmatum* rootstock (unpatented).

*Height* (*from soil line*).—280 cm at 15 years and 190 cm at 6 years.

*Width* (*horizontal plant diameter*).—180 cm at 15 years and 120 cm at 6 years.

*Growth rate.*—25 cm per year.

*Hardiness.*—Hardy from USDA Zones 4 to 8.

*Time to produce a finished tree.*—Trees are sellable at 4 years, but will also be sold at 6, 8, or 10-years-old.

*Diameter of the trunk measure at* 10 *cm from the soil line.*—10.5 cm at 15 years and 4.0 cm at 6 years.

*Trunk bark smooth at* 6 *years to slightly textured at* 15 *years.*—Small 0.1 cm to 0.4 cm wide scale-like plates RHS 156C (Greyed-White) that are variable in length and vertically arranged with jagged edges, plates separated by fissures; at 6 years fissures 0.1 cm to 0.2 cm wide and paper shallow deep, and at 15 years fissures 0.2 cm to 0.5 cm wide by up to 0.5 cm deep, fissures revealing darker-colored RHS 165B (Greyed-Orange) underlayment; no lenticels observed on the trunk.

Foliage:

*Arrangement.*—Opposite and simple.

*Quantity of leaves per lateral branch.*—Upper crown, strong lateral branches: Average is 10, 12, 14 leaves, or occasionally more. Mid-crown, moderate-sized lateral branches: Average is 6 or 8 leaves. Lower-level lateral branches: 4 or 2 leaves.

*Shape.*—Palmatilobed; 7 lobed, but occasionally, there are 9 lobes; lobes are deeply divided ½ to ¾ of the leaf.

*Apex.*—Narrowly acuminate; long, sharp leaf tip.

*Base.*—Truncate to subcordate.

*Margin.*—Doubly serrate.

*Length.*—7 cm to 10 cm.

*Width.*—7 cm to 13 cm.

*Texture* (*summer leaf*).—Upper surface: Smooth, mid-veins slightly sunken. Lower surface: Smooth, mid-veins protruding.

*Pubescence.*—Present on new foliage.

*Color, observed in August* 2022.—Immature, new leaves, both upper and lower surfaces: RHS 53A (Red). Mid-shoot, mature leaf color, both upper and lower surfaces: RHS N77A (Purple). Oldest sun-exposed leaves: Upper surface: RHS N189A (Greyed-Green). Lower surface: RHS 147B (Yellow-Green). Fall color, observed in October 2021, upper surface: Early onset and multicolored; RHS 58B (Red-Purple), RHS 51A (Red), RHS 30B (Orange-Red) and RHS 17C (Yellow-Orange).

*Petiole.*—Length: 4 cm to 7 cm. Diameter: 0.1 cm. Color: Immature or exposed upper leaf petiole: RHS 53A (Red). Mature or shaded leaf petiole: RHS N144A (Yellow-Green).

*Leaf bud.*—General: Hidden under the leaf petiole. Color: RHS N144A (Yellow-Green). Shape: Conical. Height and width: 0.1 cm and 0.1 cm.

*Venation pattern.*—Palmate, mid-lobe veins with paired forward-angled lateral veins and smaller reticulate veins.

*Venation color.*—Immature color is RHS 153A (Yellow-Green) and mature is RHS N144A (Yellow-Green); Venation color changes from immature to mature leaf and is always a lighter color compared to the base leaf color; the yellow-green highlighted venation pattern provides a glowing optic with sunlight transmission.

Lateral branches/stems:

*Quantity per tree* (*6-year-old tree*).—30 lateral branches arising from the trunk.

*Color.*—Color gradient is from red to yellow-green; new or sun-exposed branch surfaces are red and transitioning to yellow-green on shaded or aged surfaces. 1-year-old branch, sun-exposed: RHS 187B (Greyed-Purple). 1-year-old branch, mid-shoot or with some shading: RHS 181C (Greyed-Red). 1-year-old branch, base of shoot or lower shaded surface: RHS N146A (Yellow-Green). 2-year-old branch: RHS N146A (Yellow-Green).

*Size.*—Upper crown, 1-year-old shoot: 45 cm in length and 0.5 cm in width with 7 nodes. Mid crown, 1-year-old shoot: 30 cm in length and 0.3 cm in width with 5 to 6 nodes. Small, secondary 1-year-old shoot: Less than 30 cm in length and 0.1 cm in width with 1 to 3 nodes.

*Internode length.*—4 cm to 9 cm.

*Texture.*—Smooth.

*Lenticels.*—Are not a distinct visual feature; occur at the base of strong 1-year-old shoots and 2- and 3-year-old branches and are not observed on the trunk; are small, less than 0.1 cm to 0.2 cm, circular and/or diamond-shaped; lenticels have RHS 155C (White) rings surrounding a very small, and short protuberance RHS 17B (Yellow-Orange) as observed under a lens.

Flowers: Observed but not a defining characteristic of the tree.

Fruit: Each paired samara (wing and nut) is 1 cm to 1.5 cm in length and 0.5 cm to 1 cm in width with a rounded wing tip; pairs held at a wide obtuse angle 130 to 160°. Samara wing color RHS 144A (Yellow-Green) and wing edge RHS 64C (Red-Purple). The nutlet is very hard, round to oblong, 0.5 cm in width and RHS 144A (Yellow-Green). Often, only 1 of the paired nutlets has a fully developed embryo; the underdeveloped embryo has a flattened nutlet and an undersized or less than half-sized attached wing.

Disease/pest resistance: No specific disease or pest resistance has been observed to date.

COMPARISON WITH PARENTAL, COMMERCIAL AND *ACER PSEUDOSIEBOLDIANUM* AND *ACER PALMATUM* LINES

Table 1 shows a comparison of the differences between 'INAG-E61' and the commercial Maple tree 'Bloodgood' (unpatented).

TABLE 1

Comparison with Commercial Line

| Characteristic | 'INAG-E61' | 'Bloodgood' |
|---|---|---|
| Hardiness | USDA Zones 4 to 8 | USDA Zones 5 to 8 |
| Leaf lobes | 7-lobed (occasionally 9) | 5-lobed (occasionally 7) |

TABLE 1-continued

Comparison with Commercial Line

| Characteristic | 'INAG-E61' | 'Bloodgood' |
|---|---|---|
| Leaf margins | Doubly serrate | Serrate |
| Leaf venation color, mature | RHS N144A (Yellow-Green) | RHS 59B (Red-Purple) |
| Trunk 15 years | Slight texture, fissures, no lenticles | Smooth, no fissures, lenticles |
| Samara | 1 cm to 1.5 cm length and 0.5 cm to 1 cm wide | 2.5 cm to 3 cm length and 1 cm wide |

Table 2 shows a comparison of differences between 'INAG-E61' and the parental lines and Table 3 shows comparison between a typical *Acer pseudosieboldianum* and *Acer palmatum*.

TABLE 2

Comparison with Parental Lines

| Characteristic | 'INAG-E61' | Female parent: NORTH WIND 'IslNW' | Male parent-open pollinated |
|---|---|---|---|
| Hardiness zones | USDA Zones 4 to 8 | USDA Zones 4 to 8 | Not available |
| Leaf color, mature | RHS N77A (Purple) | RHS 146A (Yellow-Green) | Not available |

TABLE 3

Comparison with *Acer pseudosieboldianum* and *Acer palmatum*

| Characteristic | 'INAG-E61' | *Acer pseudo-sieboldianum* | *Acer palmatum* |
|---|---|---|---|
| Hardiness zones | USDA Zones 4 to 8 | USDA Zones 3 to 8 | USDA Zones 5 to 8 |
| Leaf color, mature | RHS N77A (Purple) | RHS 137A (Green) | RHS 147 (Yellow-Green) |
| Leaf lobes | 7 to 9 | 9 | 5 |
| Trunk | Fissured | Fissured | Smooth |
| Fall leaf drop | Yes | No, usually marcescent | yes |

I claim:

1. A new and distinct variety of Maple tree designated 'INAG-E61' as illustrated and described herein.

* * * * *